US005965160A

United States Patent [19]
Benita et al.

[11] Patent Number: 5,965,160
[45] Date of Patent: Oct. 12, 1999

[54] SELF-EMULSIFIABLE FORMULATION PRODUCING AN OIL-IN-WATER EMULSION

[75] Inventors: Simon Benita, Mevasseret Zion; Jackie Kleinstern; Tatyana Gershanik, both of Jerusalem, all of Israel

[73] Assignee: Yissum Research Development Company of the Hebrew University of Jerusalem, Jerusalem, Israel

[21] Appl. No.: 08/930,854

[22] PCT Filed: Apr. 24, 1995

[86] PCT No.: PCT/FR95/00531

§ 371 Date: Jan. 9, 1998

§ 102(e) Date: Jan. 9, 1998

[87] PCT Pub. No.: WO96/33697

PCT Pub. Date: Oct. 31, 1996

[51] Int. Cl.$^6$ .......................... A61K 9/107; A61K 9/113; A61K 9/48; A61K 9/56

[52] U.S. Cl. .......................... 424/455; 424/463; 424/490; 514/3; 514/9; 514/938; 514/943; 252/312; 252/358

[58] Field of Search .................. 514/3, 9, 938, 514/943; 424/463, 490; 252/312, 358

[56] References Cited

U.S. PATENT DOCUMENTS

| | | | |
|---|---|---|---|
| 4,464,288 | 8/1984 | Sanders | 252/312 |
| 4,592,859 | 6/1986 | Smith-Johannsen | 252/307 |
| 4,741,872 | 5/1988 | De Luca et al. | 424/487 |
| 5,160,745 | 11/1992 | DeLuca et al. | 424/487 |
| 5,256,422 | 10/1993 | Albert et al. | 424/450 |
| 5,476,660 | 12/1995 | Somasundaran et al. | 424/401 |
| 5,547,677 | 8/1996 | Wright | 424/401 |
| 5,549,901 | 8/1996 | Wright | 424/401 |
| 5,618,840 | 4/1997 | Wright | 514/549 |
| 5,677,341 | 10/1997 | Lyons | 514/558 |
| 5,744,155 | 4/1998 | Friedman et al. | 424/434 |
| 5,753,264 | 5/1998 | Magdassi et al. | 424/451 |

OTHER PUBLICATIONS

Pillarisetti Sivaram et al.; An Amino–terminal Fragment of Apolipoprotein B Binds to Lipoprotein Lipase and May Faciliate Its Binding to Endothelial Cells; The Journal of Biological Chemistry vol. 269, No.13 Issue of Apr. 1 pp. 9409–9412, 1994.

Wakerly, M.G. et al.;Evalutation of the Self–Emulsifying Performance of a Non–Ionic Surfactant–Vegetable Oil Mixture; (1986);p. 6P.

V. Stella et al.; Enhancement of Bioavailability of a Hydrophobic Amine Antimalarial by Formulation with Aleic Acid in a Soft Gelatin Capsule; Journal of Pharmaceutical Sciences vol.67 No. 10, Oct. 1978; pp. 1375–1377.

Susan A. Charman et al.;Self–Emulsifying Drug Delivery Systems: Formulation and Biopharmaceutic Evaluation of an Investigational Lipophilic Compound; Pharmaceutical Research, vol. 9, No.1, 1992.

K.J. Palin et al.; The oral absorption of cefoxitin from oil and emulsion vehicles in rats; International Journal Of Pharmaceutics 33 (1986)99–104.

Abraham Rubinstein et al.; In Vitro Release and Intestinal Absorption of Physostigmine salicylate from Submicron Emulsions; Journal of Pharmaceutical Sciences vol.80, No.7, Jul. 1991;pp. 643–647.

Robert A. Myers et al.; Systemic bioavailability of penclomedine (NSC–338720)from oil–in–water emulsions administered intraduodenally to rats; International Journal of Pharmaceutics, 78 (1992)217–226.

S.G.Barnwell et al.; Improved oral bioavailability of propranolol in healthy human volunteers using a liver bypass drug delivery system containing oleic acid; International Journal of Pharmaceutics, 88 (1992)423–432.

Efrat Elbaz et al.; Positively charged submicron emulsions—a new type of colloidal drug carrier; International Journal of Pharmaceutics, 96 (1993)R1–R6.

Ken Iseki et al.; The pH Dependent Uptake of Enoxacin by Rat Intestinal Brush–border Membrane Vesicles; J. Pharm. Pharmacol, 1992, 44; 722–726.

Hiroshi Saitoh et al.; Transport characteristics of [3H]–chlorpromazine across rat small intestinal brush border membrane; J. Pharm. Pharmacol, 1989,41: 200–202.

Colin W. Pouton et al.; Self–Emulsifying Systems for Oral Delivery Of Drugs; Proceed, Intern. Symp. Control.Ref. Bioact. Mater. 14 (1987); pp. 113–114.

Handbook of Emperimental Pharmacology;vol. 70/I; Germany, 1984 pp. 324–325.

S. Benita et al.; Micronized Emulsion for Controlled Release of Physostigmine After Oral Administratiom, Part II. Release Characteristics and Pharmacological Evaluation; Drug Design and Delivery, 1989, vol.4, pp. 143–153.

D. Friedman et al.; Micronized Emulsion For Controlled Release Of Physostigmine After Oral Administration. Part I. Formulation Design; Drug and Delivery, 1989, vol. 4, pp. 135–142.

C.W. Pouton; Effects of the Inclusion of a Model Drug on the Performance of Self Emulsifying Formulations; (1984) J. Pharm. Pharmac. 36: 51P.

Mark G. Wakerly et al.; Self–Emulsification of Vegetable Oil–Nonionic Surfactan Mixtures; 1986 American Chemical Society; pp. 242–255.

Colin W. Pouton; Self–emulsifying drug delivery systems; assessment of the efficiency of emulsification; International Journal of Pharmaceutics, 27 (1985) 335–348.

*Primary Examiner*—Shep K. Rose
*Attorney, Agent, or Firm*—Helfgott & Karas, P.C.

[57] ABSTRACT

A self-emulsifying oily formulation (SEOF) comprising an oil component and a surfactant, the SEOF being characterized in that the oil component comprises an oily carrier and a cationic lipid and optionally, a lipophilic oily fatty alcohol, the oil-in-water emulsion which forms upon mixture of the SEOF, having oily droplets which are positively charged.

22 Claims, 6 Drawing Sheets

SELF-EMULSIFIABLE FORMULATION PRODUCING AN OIL-IN-WATER EMULSION

This application is a 371 of PCT/FR95/00531 filed Apr. 24, 1995.

FIELD OF THE INVENTION

The present invention concerns a self-emulsifying essentially hydrophobic formulation, namely, a formulation which upon mixture with water, spontaneously disintegrates to form an oil-in-water emulsion. The present invention also concerns the pharmaceutical use of such a formulation both (i) as a drug delivery vehicle of a lipophilic drug or (ii) as a precursor for the preparation of an oil-in-water emulsion useful in turn as a drug delivery vehicle of hydrophobic drugs.

One application of the inventive formulation is in the oral administration of a drug intended to be absorbed in the gastro intestinal (GI) tract and then reach the target organ via the blood or lymphatic system. Such a form of administration will be referred to herein as "oral systemic administration".

A particular application of the above preferred embodiment is in the oral systemic administration of a drug such as physostigmine, probucol, cyclosporin A, morphine base, penclomedine, and others.

The acknowledgement herein of the above prior art should not be interpreted as an admission that this art is in any way relevant to the issue of patentability of the invention as defined herein.

BACKGROUND OF THE INVENTION

Oral systemic administration of drugs, in general, is the preferred mode of administration in ambulatory treatment regimens which require repetitive drug administration over periods of time. While oral systemic administration is very effective with respect to water soluble drugs, it proves to be a problematic administration route for hydrophobic drugs or drugs with limited aqueous solubility such as physostigmine base, isradipine, virginiamycine, cyclosporin A, morphin, buprenorphine, nalorphine, methorfan, probucol and others.

The poor systemic effect achieved with orally-administered hydrophobic drugs results from a number of factors. For one, hydrophobic drugs do not dissolve in water and form a separate phase in aqueous solutions and are thus not readily available for absorption through the walls of the GI tract. Furthermore, some hydrophobic drugs, which are absorbed primarily through the walls of the small intestine, particularly through the jejunum, may undergo a so-called "first pass effect", i.e passage of the drugs in the liver prior to reaching the blood system. The overall effect of these factors is that only low, often non effective, amounts of orally administered hydrophobic drugs eventually reach the target organ(s), i.e orally administered hydrophobic drugs have generally a low bioavailability. This may be overcome by increasing the dose of the drug, but such an increase may, however, result in increased incidence of side-effects owing to erratic and variable inter subject absorption.

There have been various proposals for increasing bioavailability of hydrophobic drugs. For example, previous studies using oleic acid containing a dissolved lipophilic drug, have demonstrated a beneficial effect on drug bioavailability (Stella et al, 1978, J. Pharm. Sci, 67, 1375–1377). Recently, it was shown that the bioavailability of propranolol following oral administration, can be improved by dissolving the drug in a lipid formulation containing mainly oleic acid and packing it into a sealed and entero-coated hard gelatine capsule (Barnwell et al, 1992, Int. J. Pharmaceutics, 88, 423–432).

Emulsions have been proposed as carriers in oral formulations of hydrophobic drugs in general (Pal et al, 1984, J. Int. Pharm, 33. 99–104; Myers et al, 1992, Int. J. Pharm. 78, 217–226) and for drugs such as physostigmine in particular (Rubinstein et al, 1991, J. Pharm. Res, 80, 643–647; Friedman et al, 1989, Drug Design and Delivery, 4, 135–142; Benita et al, 1989, Drug Delivery Design, 4, 143–153). Colloid particles of the emulsion which carry the drug are absorbed in the jejunum and are presumably carried away mainly by the lymph through the thoracic duct, thus bypassing the liver and greatly reducing the first pass effect. Indeed, the oral bioavailability of several lipophilic drugs was shown to be somewhat improved using emulsions as vehicles for their oral systemic administration.

However, in many cases emulsion formulations offered no improvement in the bioavailability of hydrophobic drugs versus their administration in aqueous formulations. This is particularly the case with respect to drugs such as physostigmine, which is an amphiphilic drug that localizes in the emulsion in the oil/water (o/w) interfacial film of the emulsion colloid particles. During passage of an emulsion containing physostigmine through the digestive tract, the emulsion, which is practically infinitely diluted, quickly releases the drug contained therein. This problem is increasingly augmented by the very strong acidity in the stomach which has a tendency to reduce the stability of the emulsion's colloid particles.

Certain lipid solutions, by virtue of their ingredients, have the capacity to undergo spontaneous emulsification when introduced into an aqueous phase following gentle agitation yielding oil-in-water emulsions. Such lipid solutions are defined in the literature as self-emulsifying delivery systems (Charman et al, 1992, Pharm. Res, 9, 87–93). Self-emulsifying delivery systems have been formulated using medium-chain triglyceride oils and nonionic surfactants which, depending on their exact nature, could form the basis of a self-emulsifying drug delivery system (Pouton, 1985a, Int. J. Pharm. 27, 335–348; Pouton 1985b, Int. J. Pharm. 37, 1P; Pouton et al, 1987, Proc. Int. Symp. Control. Rel. Bioacta. Mater, 14, 113–117; Wakerly et al, 1986, ACS. Symp. Ser. 311, 242–255; Wakerly et al, 1987, J. Pharm. Sci, 67, 1375–1377). These formulations may be encapsulated in soft gelatine capsules or sealed hard gelatin capsules to yield precise and convenient unit dosage systems.

Early studies in the small intestine clearly established, that the absorptive cell interior is negative with respect to mucosal solution (Csaky, Ill. (Ed.), Handbook of Experimental Pharmacology, Vol 70, Springer-Verloy, Berlin, (1984), 324–325). It has also been reported that some hydrophobic cationic drugs, completely ionized over the pH range of the GI tract, are absorbed rapidly, in spite of their poor water solubility (Iseky, K, Hirano, T, Fukushi, Y, Kitamura, Y, Miyazaki, S, Takada, M; Sugawara, M, Saiton, H and Miyazaki, K. (1992), J. Pharm. Pharmacol, 44:9, 722–726; Saiton, H, Kawai, S, Iseki, K, Myazaki, K and Arita, T. (1988), J. Pharm. Pharmacol, 41, 200–202). Moreover, some endogenic compounds bind to endothelial surfaces by its NH2-terminal, indicating physiological importance of the electrostatic interactions (21).

The formation of oily droplets containing a dissolved drug brings about distribution of the drug throughout the GI tract while providing a large interfacial area for partitioning of the drug between the oil and the surrounding aqueous phase. Thus, for drugs with limited aqueous solubility, which are poorly absorbed in the GI tract, the spontaneous disintegration of the lipid phase into very fine dispersed oily droplets may offer an improvement in both the rate and extent of absorption. All the self-emulsifying drug delivery systems known to date, contain large concentrations of surfactants (up to 50%) which were either non-ionic (such as Tween(R), Span(R)) or anionic surfactants (such as phospholipids) resulting in the formation of oily droplets having either a neutral or an electronegative charge.

In a recent report (Elbaz et al, 1993, Int. J. Pharm. 96, R1–R6) an emulsified drug delivery system has been disclosed in which the colloid particles bear a positive charge. However, no mention was made in this publication to the possibility of using such emulsions as an oral systemic drug delivery vehicle.

It is an object of the present invention toprovide a self-emulsifying formulation useful as a drug delivery system of lipophilic drugs.

It is a further object of the invention to provide a novel drug delivery system for the systemic oral administration of lipophilic drugs.

It is yet another object of the invention to provide a novel method for the administration of lipophilic drugs.

It is yet still a further object of the invention to provide a method for production of an emulsion by the use of a self-emulsifying oily preparation.

GENERAL DESCRIPTION OF THE INVENTION

In accordance with the invention, a novel self-emulsifying oily formulation (SEOF) is provided. When the formulation of the invention is mixed with an aqueous solution, and the mixture is agitated, an oil-in-water emulsion is formed. According to a preferred embodiment of the invention the droplets in the so-formed emulsion have a diameter below about 0.2 $\mu$m. Emulsions having tiny droplets as those obtainable in accordance with the invention, were hitherto obtainable only by employing a complex homogenization procedure involving the use of intricate equipment (see for example Benita et al, 1989, Drug Delivery Design, 4, 143–153).

An additional feature of the SEOF of the invention is that the droplets in the formed emulsion are positively charged, unlike the negatively charged emulsions achieved with prior art SEOF.

The SEOF of the invention comprises an oily carrier which may be a medium chain triglyceride (MCT) oil, a long chain triglyceride (LCT) oil, and an oily fatty acid derivative. In addition, the SEOF comprise also a cationic lipid. It has been found in accordance with the invention that the addition of a lipophilic alcohol is required for obtaining emulsion droplets in the submicron (<1 $\mu$m) range. The inclusion of a lipophilic alcohol in the SEOF of the invention is thus preferred.

The present invention thus provides a self-emulsifying oily formulation (SEOF) comprising an oil component and a surfactant, the SEOF being characterized in that the oil component comprises an oily carrier and a cationic lipid and optionally, a lipophilic alcohol, the oil-in-water emulsion which forms upon mixture of the SEOF, having oily droplets which are positively charged.

The SEOF of the invention can be used as a delivery vehicle for hydrophobic drugs. When such a delivery vehicle, with the drugs dissolved therein, comes into contact with a body fluid, it spontaneously emulsifies forming tiny oily droplets with the drug contained therein.

One specific example of such a drug delivery vehicle is one which is intended for the oral systemic administration of hydrophobic drugs. For such administration, the SEOF with the dissolved drugs are preferably encapsulated.

The present invention thus provides a pharmaceutical preparation comprising an effective amount of a hydrophobic drug dissolved in a liquid carrier, the preparation being characterized in that said carrier is the above SEOF. Specific embodiments of said preparation is oral systemic preparations.

The term "effective amount" should be understood as meaning a dose of the drug effective in exerting a therapeutic effect. For an oral preparation of the invention, the term "effective amount" means a dose of the drug which after its absorption into the body through the walls of a GI tract, yield a drug concentration in the blood which is effective in exerting a therapeutic effect on a target organ.

The invention also provides a method for administration of a hydrophobic drug, to locations in the body, e.g GI tract, into the blood, etc . . . , where the preparation comes into contact with body fluids, comprising administering the drug in an oily vehicle being the above SEOF.

Another use of the SEOF of the invention is in a process for the production of emulsions, particularly such having droplets in the submicron range (submicron emulsions). A specific embodiment in the preparation of emulsions comprising a hydrophobic drug and intended to be used as pharmaceutical preparations. Thus, the present invention provides a process for the production of an emulsion, comprising mixing said SEOF with an aqueous solution and agitating the mixture. Where the emulsion is to be used as a carrier of hydrophobic drugs, the SEOF will have said drug dissolved therein.

DETAILED DESCRIPTION OF THE INVENTION

In accordance with the invention, a novel self-emulsifying oily formulation has been prepared. This SEOF may be used in pharmaceutical preparations as a carrier of hydrophobic drugs or may be used as a precursor for the preparation of emulsions, particularly submicron emulsions.

The SEOF of the invention comprises a surfactant and an oil component comprising a cationic lipid and at least one of MCT, LCT and an oily fatty acid derivative. The oil component comprises an oily fatty alcohol as an optional ingredient. In addition, the oil component may also comprise other ingredients as will be specified below. Obviously, all ingredients used should be physiologically compatible.

MCT oil is a triglyceride oil in which the carbohydrate chain has an average of about 8–12 carbon atoms. Examples of MCT oils are TCM™ (Societe des Oleagineux, France) which is a mixture of triglycerides wherein about 95% of the fatty acid chains have either 8 or 10 carbon atoms; or MYGLYOL 812™ (Dynamit Nobel, Sweden) which is a mixture of triesters of glycerine and of caprylic and capric acid.

LCT oil is a triglyceride oil in which the carbohydrate chain has an average chain length above 12 carbon atoms. Examples of LCT oils which can be used in accordance with the present invention are arachis oil, safflower oil, sesame oil, soybean oil, cotton seed oil, olive oil.

Oily fatty acid derivatives may be various lipophilic substituted fatty acids, e.g esters with alkyl alcohols, examples being methyl or ethyl esters of fatty acids, such as ethyl oleate.

Cationic lipids are lipids which have a positively charged polar group. Examples of cationic lipids are $C_{10}$–$C_{24}$ fatty alkylamines and $C_{12}$–$C_{24}$ fatty alkanoylamines, $C_{12}$–$C_{18}$ fatty alkylamines and $C_{12}$–$C_{18}$ fatty alkanoylamines being preferred. Specific examples of cationic lipids are stearylamine and oleylamine. In addition to cationic lipids, the oil component may also comprise cationic surfactants such as cationic cholesterol ester and cationic cholesterol derivatives, e.g cholesterol betaïnate.

Oily fatty alcohols include various lipophilic alcohols such as fatty acid alcohols, e.g, oleyl alcohol, or aryl alcohols, e.g, benzyl alcohol, ethyl alcohol or any other lipophilic non-toxic alcohol.

In addition to the above ingredients, said oil component may also comprise various other oily ingredients including other types of vegetable oil, mineral oil and isopropyl myristate. In addition, the oil component may also comprise neutral or anionic lipids, the amount of the anionic lipids being such so as not to fully eliminate the positive charge of the emulsion droplets.

The surfactant used in the SEOF of the invention may be any of those known per se. The surfactant is preferably a non-ionic surfactant and may, for example, be Tween, e.g Tween 80 and Tween 85; Span, e.g Span 80; or a glycosylated polyoxyethylenized glyceride, e.g LABRAFIL M 1944 CS™ (Gattefosse Corp, USA). Other examples of non-ionic surfactants are esters of sorbitol and fatty acids such as sorbitan monoleate, and oily sucrose esters such as sucrose mono-, di-, or tri-palmitate. In addition to non-ionic surfactants also ionic surfactants such as phospholipids may be used, the amount of such ionic surfactants should be such so as not to eliminate the positive charge of the emulsion droplets. At times it is useful to use a combination of different surfactants such as a combination of Tween 80 and Span 80 or Tween 85 and Span 80.

Typical pharmaceutical application of the SEOF of the invention is in oral systemic administration of hydrophobic drugs. For this administration the SEOF with the drug dissolved therein will preferably be encapsulated in sealed soft or hard gelatin capsule. The capsule is typically of a kind which is dissolved in a particular region of the GI tract releasing its content there. An example of such a capsule is an entero-coated soft or hard gelatin capsule. Enteric coating, as known per se, is a coating with a substance or a combination of substances that resists dissolution in gastric fluid but disintegrates in the intestine. Examples of enteric coatings are hydroxypropylmethylcellulosophthalate B.P. As a result of the enteric coating, the capsule is resistant to dissolution in upper parts of the digestive tract and thus dissolves only in the intestine, e.g as a result of contact with bile acids and salts in the jejunum. Emulsion droplets particularly such comprising LCT, e.g soybean oil, are likely absorbed in the jejunum via the lymphatic system in chylomicrons which are carried away from the small intestine through the thoracic duct, thus bypassing the liver. Such an absorption route thus significantly reduces the first pass effect of drug degradation in the liver.

Commercially available capsules range in size up to such having an internal volume of about 0.7 ml. From experiments carried out in accordance with the present invention it became evident that this volume is sufficient for the delivery of an effective amount of drug, such as physostigmine, so as to achieve a systemic effect.

For pharmaceutical use of the SEOF of the invention preservatives such a methyl paraben, propyl paraben, butyl paraben or a combination of these, as well as anti-oxidants such as propyl gallate, BHT or dimercaprol can be used. Furthermore, prior to use, the preparation is preferably sterilized by filtration.

The invention will now be further illustrated in the following examples and the annexed drawing.

EXPERIMENTAL METHODS (i) Particle Size Evaluation:

Particle droplet size of disintegrating SEOF was determined using a super nanosizer apparatus (Coulter N4) in which the particle sizes are evaluated by a photon correlation spectroscopy. Prior to evaluation, the preparations were diluted using filtered and sonicated 2.25% glycerin solution.

(ii) Emulsion Charge:

The charge on the emulsion was determined by electrophoretic mobility. A standard negatively charged fat emulsion, Intralipid$^{(R)}$ (Kabi-Vitrum, Sweden) immersed in 2.25% glycerin solution moves in the direction of the positive electrode due to the negative charge of the dispersed oil droplets. The various emulsified oil formulations (in gastric or intestinal fluid, USP) migrated in the opposite direction towards the negative electrode validating the positive charge on the oil droplets.

(iii) Zeta-Potential:

The zeta-potential was measured using the moving boundary electrophoresis technique. The zeta-potential value of the spontaneously formed oil droplets was determined using a Zetasizer™ (DELSA 440 Coulter) using a 2.25°/°° glycerin solution as diluent.

(iv) Visual Observations:

The degree of stability of the SEOF formulation and the degree of the phase separation in the emulsion derived from such formulations was assessed visually at given time intervals. Any visible change was recorded.

EXAMPLE I

SEOF Preparation

The SOEFs were prepared by the following steps:
1. The fatty alcohol and most of the oily carrier were mixed in a flask
2. A surfactant was then added and solubilized by stirring
3. The cationic lipid was then added and dissolved in the above mixture. In the case of stearylamine, a light heating to about 37° C. was required in order to solubilize this ingredient.
4. The final weight of the composition was completed by the addition of the remaining oily carrier.
5. The drug may be dissolved either in fatty alcohol prior its addition to the mixture or added after incorporation of other ingredients of the formulation before completing to the final weight with the oily carrier.
6. Only in examples VI–X drug was included. Examples II–V contained no drug.

For emulsion formation the prepared SEOF was mixed with double distilled water or simulated USP gastric and intestinal fluids.

EXAMPLE II

SEOFs which disintegrate into oil droplets having a diameter less than 250 μm

A range of SEOFs was prepared from the following ingredients: Span, Tween 85, Stearylamine and arachis oil. The following Table lists these four ingredients showing the tested concentration range and the preferred concentration range and a typical concentration for each ingredient which yields a minimal particle size.

TABLE I

| Ingredient | Preferred Conc. (%, w/w) | Conc. Range (%, w/w) | Typical Conc. (%, w/w) |
|---|---|---|---|
| Span 80 | 25–30 | 15–40 | 25 |
| Tween 85 | 4–5 | 1–10 | 3 |
| Stearylamine | 2.5–3 | 1–3 | 3 |
| Arachis oil | | | to 100 |

Each of the formulation was transparent in liquid at 37° C. and became opalescent and viscous at room temperature. The emulsions which were formed from these formulations, remained stable at room temperature for a few hours. The particle size of the oil droplets in the emulsions following gentle agitation ranged from 50 to 250 μm.

In addition to arachis oil, other LCT oils including safflower oil, sesarrie oil, soybean oil, cotton seed oil and olive oil were tested. Emulsions within the above range (50–250 μm) were achieved with all these LCT oils. Optimal emulsions, having droplets at the lower end of the above range were obtained with arachis and safflower oils.

In addition, also MCT oil was tested in place of arachis oil and showed to yield also droplets of a size within the same range.

EXAMPLE III

SEOFs which disintegrate into-submicron oil droplets

SEOFs were prepared from the following ingredients: Tween 80, Span 80, oleyl alcohol, oleyl amine and ethyl oleate. The ingredients of a typical formulation, the tested concentration range for each ingredient, the preferred concentration range and a typical concentration yielding droplets of minimal size are shown in the following Table II.

TABLE II

| Ingredient | Preferred Conc. (%, w/w) | Conc. Range (%, w/w) | Typical Conc. (%, w/w) |
|---|---|---|---|
| Tween 80 | 25–30 | 15–40 | 25 |
| Span 80 | 1.5–2 | 0.5–3 | 1.5 |
| Oleyl alcohol | 5–8 | 0–10 | 7.5 |
| Oleyl amine | 2–2.5 | 1–3 | 2.5 |
| Ethyl oleate | | | to 100 |

The droplet size is of the emulsions which were formed from these SEOFs ranged in diameter between 160 to 200 nm with a standard deviation of 60–70 nm. The oily droplets were positively charged.

The emulsions were all stable at room temperature for several weeks.

The concentration of oleyl alcohol in the lipid solution was found to affect the final droplet size. The results are shown in the following Table III.

TABLE III

| Oleyl alcohol conc. (%, w/w) | Droplet diameter (nm) |
|---|---|
| 5 | 160 ± 60 |
| 10 | 200 ± 63 |
| 12.5 | 650 ± 900 |

When Tween 85 was used instead of Tween 80, an increase in concentration of oleylamine up to 7–8% was needed to achieve a positive emulsion. The final particle size of the resulting dispersed droplets in this case ranged from 1 to 2 μm.

Ethyl oleate was the only solvent of those tested which was able to produce emulsions in the submicron range.

EXEMPLE IV

SEOFs which disintegrate into oil droplets ranging from 20 to 200 nm

SEOFs were prepared from the following ingredients: Tween 80, benzyl alcohol, oleyl amine and ethyl oleate. The ingredients in the tested concentration range of each are shown in the following Table IV.

TABLE IV

| Ingredients | Conc. Range (%, w/w) |
|---|---|
| Tween 80 | 25–40 |
| Benzyl alcohol | 0.5–50 |
| Oleyl amine | 2.5 |
| Ethyl oteate | to 100 |

A formulation of which contained less than 0.5% benzyl alcohol was not stable. When more than 50% benzyl alcohol was included, no stable submicron emulsion was achieved.

The following Table V shows the particle size as a function of Tween 80 and Benzyl alcohol concentration (under constant dilution with the aqueous phase of 1:1).

TABLE V

| | | | | | | |
|---|---|---|---|---|---|---|
| Tween 80 (%, w/w) | 25 | 25 | 25 | 25 | 35 | 40 |
| Benz. Alc. (%, w/w) | 5–12 | 25 | 37.5 | 50 | 45 | 40 |
| Particle size (nm) | 191 ± 60 | 175 ± 63 | 110 ± 38 | 86 ± 30 | 37 ± 14 | <12 |

As can be seen, the smallest droplet diameter was achieved with a 40% Tween 80 and a 40% Benzyl alcohol formulation.

Figure 1:
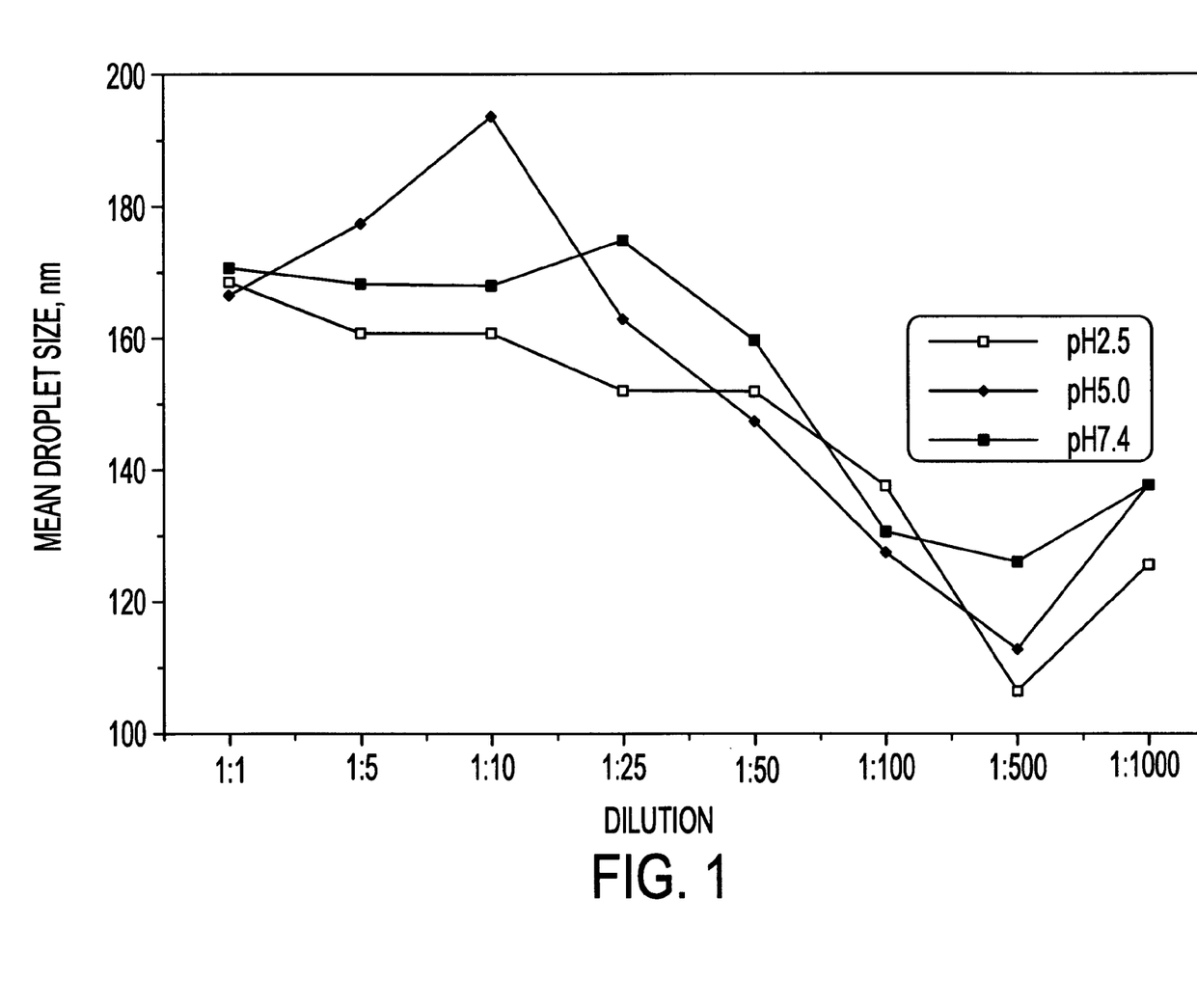
FIG. 1: shows the mean droplet size as a function of the level of dilution of the SEOF in an aqueous phase. The SEOF consisted of 25% Tween 80, 12.5% Benzyl alcohol, 2.5% Oleylamine and Ethyl oleate to ~100%. The particulars of these experiments are described in example IV.

FIG. 1 shows results obtained with a SEOF which consisted of 25% Tween 80, 12.5% benzyl alcohol, 2.5% oleylamine and ethyl oleate added to a total of 100%. As can be seen in FIG. 1, the particle size decreased with increased aqueous phase dilution until dilution of about 1:500. Further dilution to 1:1000 brought to a slight increase in the droplet size.

Figure 2:
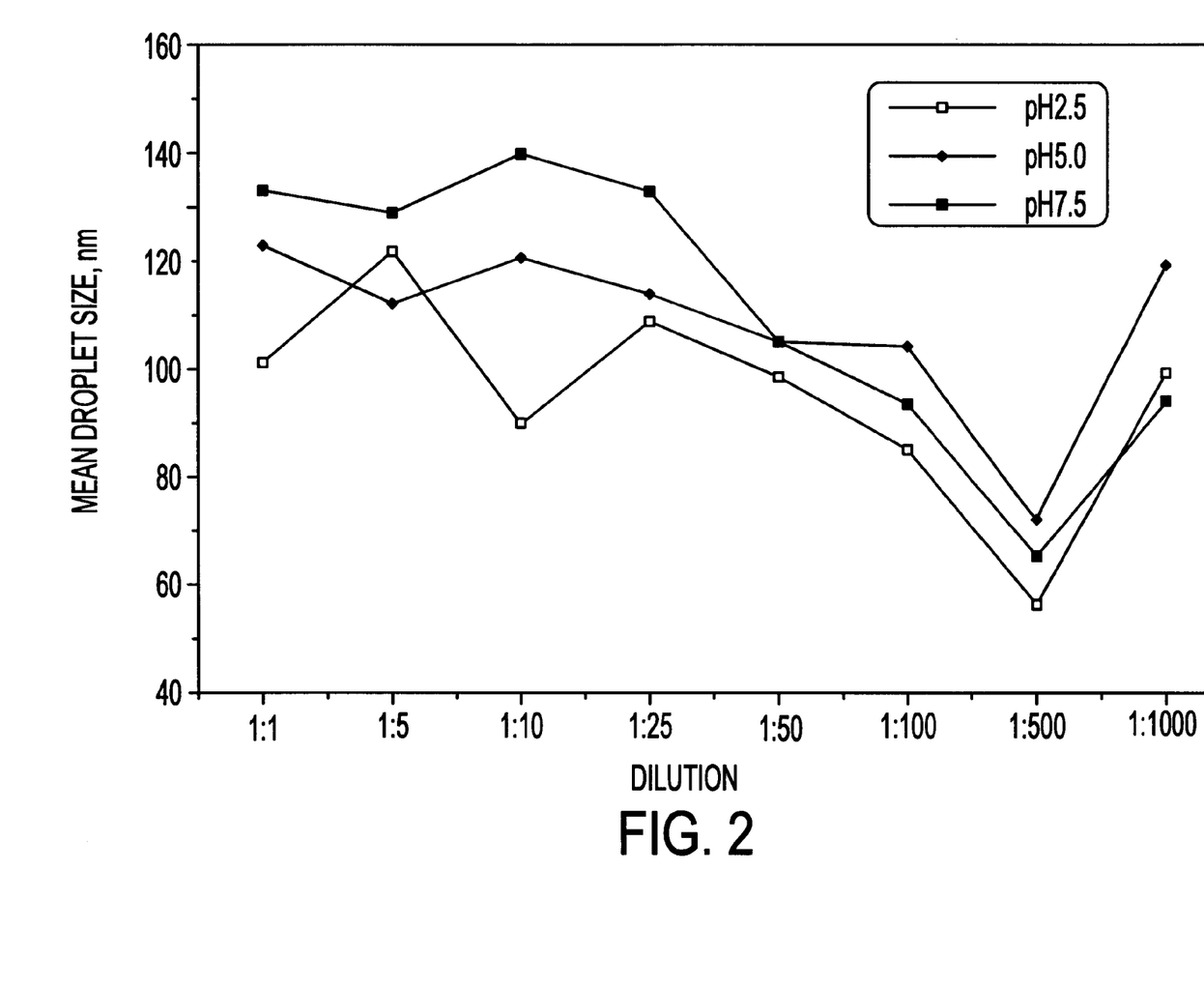
FIG. 2: shows the results of a similar experiment to that shown in FIG. 1, also reported in example IV, with the difference being in that the Tween 80 concentration was 35%.

As can be seen in FIG. 2, the same type of behavior was also seen with a different SEOF comprising 35% Tween 80 instead of 25% as in the SEOF of FIG. 1.

FIG. 1, FIG. 2 and table VI demonstrate, that effective self-emulsification does not show high pH dependency, but some tendency of droplet size enlarging as a function of pH increase was observed.

Influence of pH on mean droplet size as a function of pH and time.

TABLE VI

| pH  | dilution | 0 day    | 1 day    | 7 days   | 34 days    |
|-----|----------|----------|----------|----------|------------|
| 2.5 | 1/500    | 105 ± 36 | 113 ± 25 | 120 ± 33 | 137 ± 45   |
|     | 1/1000   | 125 ± 45 | 127 ± 37 | 134 ± 42 | 157 ± 52   |
| 5.0 | 1/500    | 112 ± 34 | 120 ± 36 | 125 ± 36 | 136 ± 43   |
|     | 1/1000   | 130 ± 46 | 139 ± 46 | 150 ± 44 | 157 ± 52   |
| 7.4 | 1/500    | 127 ± 44 | 137 ± 44 | 145 ± 44 | 198 ± broad|
|     | 1/1000   | 137 ± 48 | 146 ± 52 | 151 ± 56 | 188 ± broad|

Figure 3:
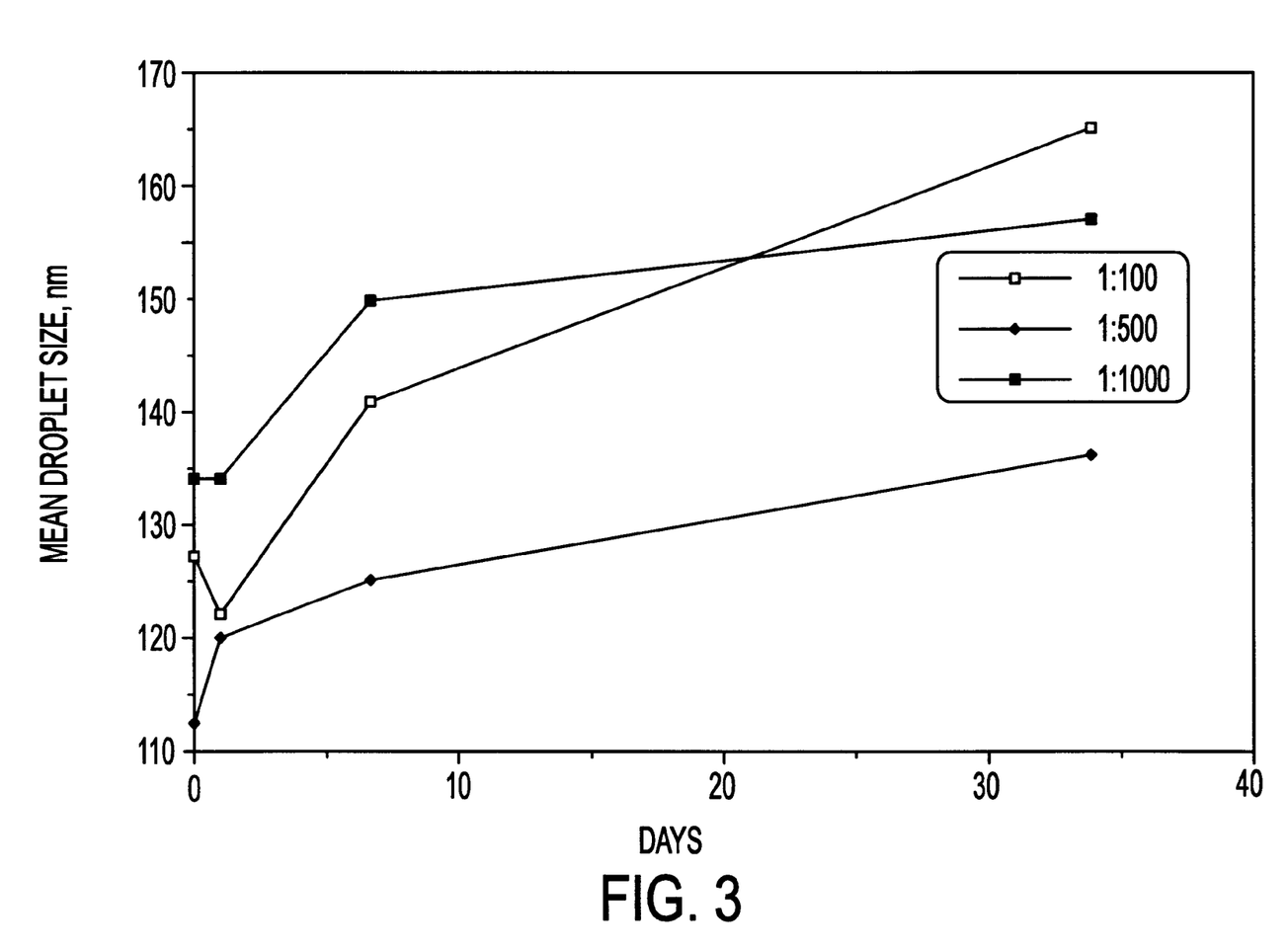
FIG. 3: shows the results of an experiment, described in example IV, in which the mean droplet size was tested over time in three different dilutions of the SEOF in an aqueous phase. The SEOF consisted of 25% Tween 80, 12% Benzyl alcohol, 2.5% Oleylamine and Ethyl oleate ~100%. The pH level of the aqueous phase was 5.0.
Figure 4:
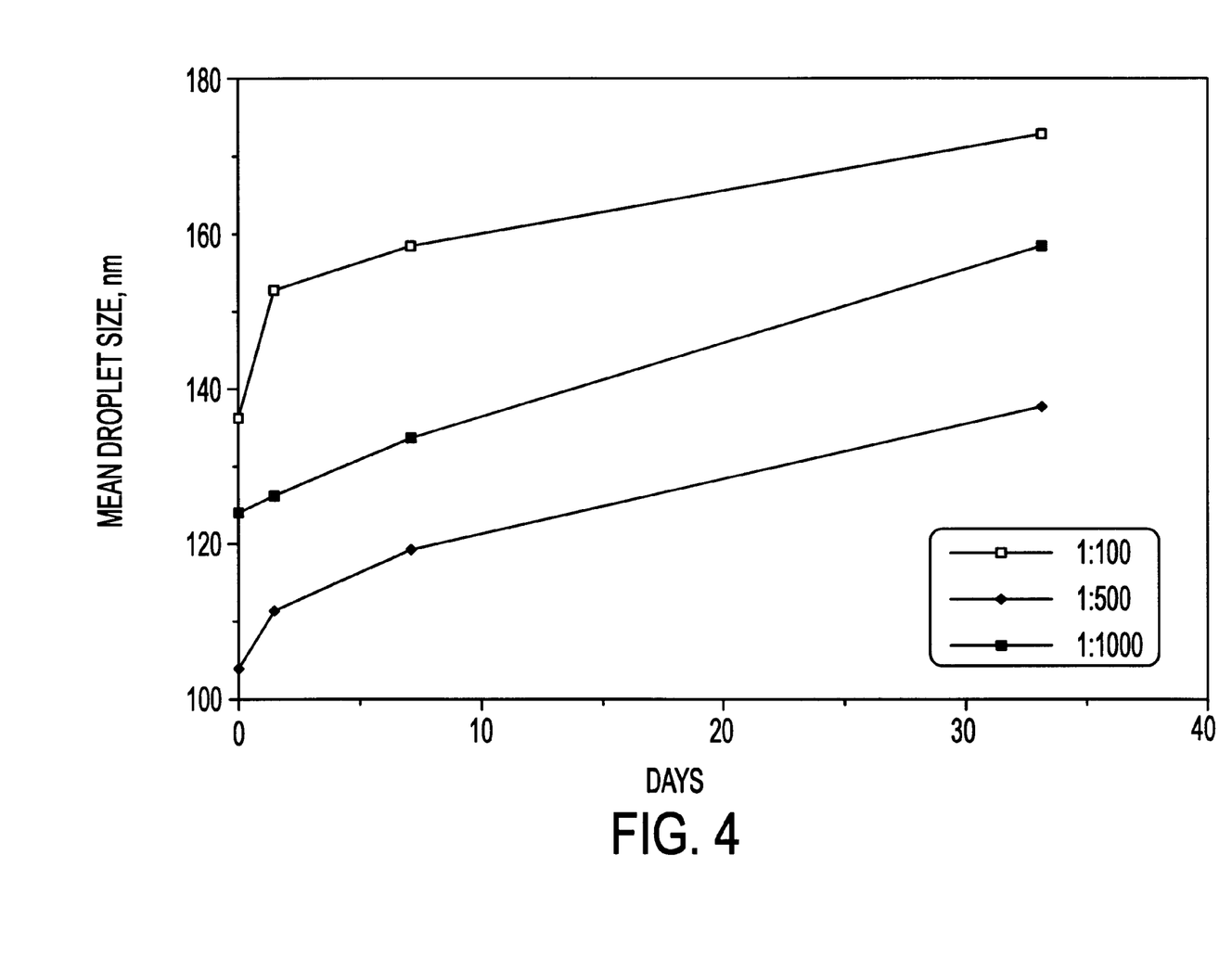
FIG. 4: shows the results of a similar experiment to that of FIG. 3, also described in example IV, with the difference being in that the pH level of the aqueous phase was 2.5. (adjusted with phtala buffer)

Reference is made to FIGS. 3 and 4 showing results from an experiment in which the stability of emulsions, as reflected by their mean droplet size, was tested over time. The SEOF in both cases consisted of 25% Tween 80, 12.5% benzyl alcohol (BA), 2.5% oleylamine (OA) and ethyl oleate (EO) added to 100%. In the experiment shown in FIG. 3, the pH was 5.0 whereas the pH in the experiment of FIG. 4 was 2.5. As can be seen, the emulsions which were formed were stable for over 30 days under the tested conditions. It should be noted that under a dilution of less than 1:100, the emulsions were stable for only about one week. Furthermore, under a pH of the aqueous phase of above 7.4, the emulsions were also stable for a period of only one week.

EXEMPLE V

Zeta-potential of the droplets, produced from SEOF

The quantitative Zeta-potential measurements have been composed with emulsions, prepared from SEOF, that were described in example 3. The emulsions comprised different amounts of Oleylamine (0.5%). Table VII shows zeta-potentials of these emulsions, the emulsions resulting from the dilution of the SEOF (1:10) comprised different amounts of oleylamine (0–0.5%), measured in 2.25% glycerin solution. As can be seen, SEOF, that included Oleylamine were capable of producing droplets, bearing a positive charge.

TABLE VII

Zeta potential measurements of emulsions produced by dilution of SEDDS with 2.25% glycerin solution

|          | Formulation (%, w/w) | Zeta-potential value at 25° C. (mV) |
|----------|----------------------|--------------------------------------|
| Tween 80 | 25                   | −8.4                                 |
| BA       | 12.5                 |                                      |
| EQ       | to 100               |                                      |
| Tween 80 | 25                   | +15.8                                |
| BA       | 12.5                 |                                      |
| OA       | 2.5                  |                                      |
| EQ       | to 100               |                                      |

TABLE VII-continued

Zeta potential measurements of emulsions produced by dilution of SEDDS with 2.25% glycerin solution

|          | Formulation (%, w/w) | Zeta-potential value at 25° C. (mV) |
|----------|----------------------|--------------------------------------|
| Tween 80 | 25                   | +33.3                                |
| BA       | 12.5                 |                                      |
| OA       | 5                    |                                      |
| EO       | to 100               |                                      |

EXAMPLE VI

SEOFs with the Drugs

Physostigmine, cyclosporin A, probucol and insulin (insulin was finely dispersed in the oil formulation by sonication for 5 min using a bath sonicator) were incorporated into SEOFs and the formulations are shown in the following Table VIII

TABLE VIII

|   | Ingredients              | Conc. (%, w/w) |
|---|--------------------------|----------------|
| 1 | Physostigmine Salicylate 0.6% | 25%       |
|   | Span 80                  | 25%            |
|   | Tween 85                 | 5%             |
|   | Stearylamine             | 3%             |
|   | Arachis oil              | to 100%        |
| 2 | Cyclosporine A           | 5%             |
|   | Tween 80                 | 25%            |
|   | Span 80                  | 1.5%           |
|   | Oleyl alcohol            | 7.5%           |
|   | Oleyl amine              | 2.5%           |
|   | Ethyl oleate             | to 100%        |
| 3 | Probucol                 | 4%             |
|   | Tween 80                 | 25%            |
|   | Benzyl alcohol           | 50%            |
|   | Oleyl amine              | 2.5%           |
|   | Ethyl oleate             | to 100%        |
| 4 | Insulin                  | 0.5%           |
|   | Tween 80                 | 25%            |
|   | Benzyl alcohol           | 12.5%          |
|   | Oleyl amine              | 2.5%           |
|   | Ethyl oleate             | to 100%        |
| 5 | Progesterone             | 10%            |
|   | Tween 80                 | 25%            |
|   | Benzyl alcohol           | 30%            |
|   | Oleyl amine              | 2.5%           |
|   | Ethyl oleate             | to 100%        |

EXAMPLE VII

Inhibition of Cholinesterase by Orally Administered Physostigmine in rats

The pharmacological effect of orally administered physostigmine (PS) on rats was tested by a modification of a method previously reported by Steffens (Steffens A. B 1969, Physiology and Behavior, 4, 833–836). Male Sabra rats were cannulated chronically through the jugular vein one day prior to experimentation allowing frequent blood sampling from a non-anaesthetized rat. Each group of awake rats (3–4 animals in each group) were administered per os (PO) with one of three PS formulations. All formulations were administered at a dose of PS of 0.5 mg/kg. 0.1 ml blood samples were taken at specific time intervals up to five hours following the drug administration and analyzed for cholinesterase activity according to the radiometric assay of Johnson & Russel (Johnson C. D and Russel R. L., 1975, Anal. Biochem, 64, 229–238).

The tested formulations were the following:

Formulation 1:
9 mg P.S, 8.5 gm soybean oil, 8.5 gm oleic acid, 1.0 gm labrafil M1944Cs, 0.02 gm isopropyl gallate, 0.02 gm PHT, 0.02 gm dimercaptol and 0.02 gm butyl paraben.

Formulation 2:
5 mg P.S, 1 ml Ethanol (95%), 1.0 gm Lipoid-E80, 0.02 gm α-Tocopherol, 0.21 gm stearylamine and 8.0 gm soybean oil.

Formulation 3:
6 mg P.S, 3 mg Span 80, 0.6 gm Tween 85, 0.36 gm Stearylamine and Arachis oil to 12 gm.

Figure 5:
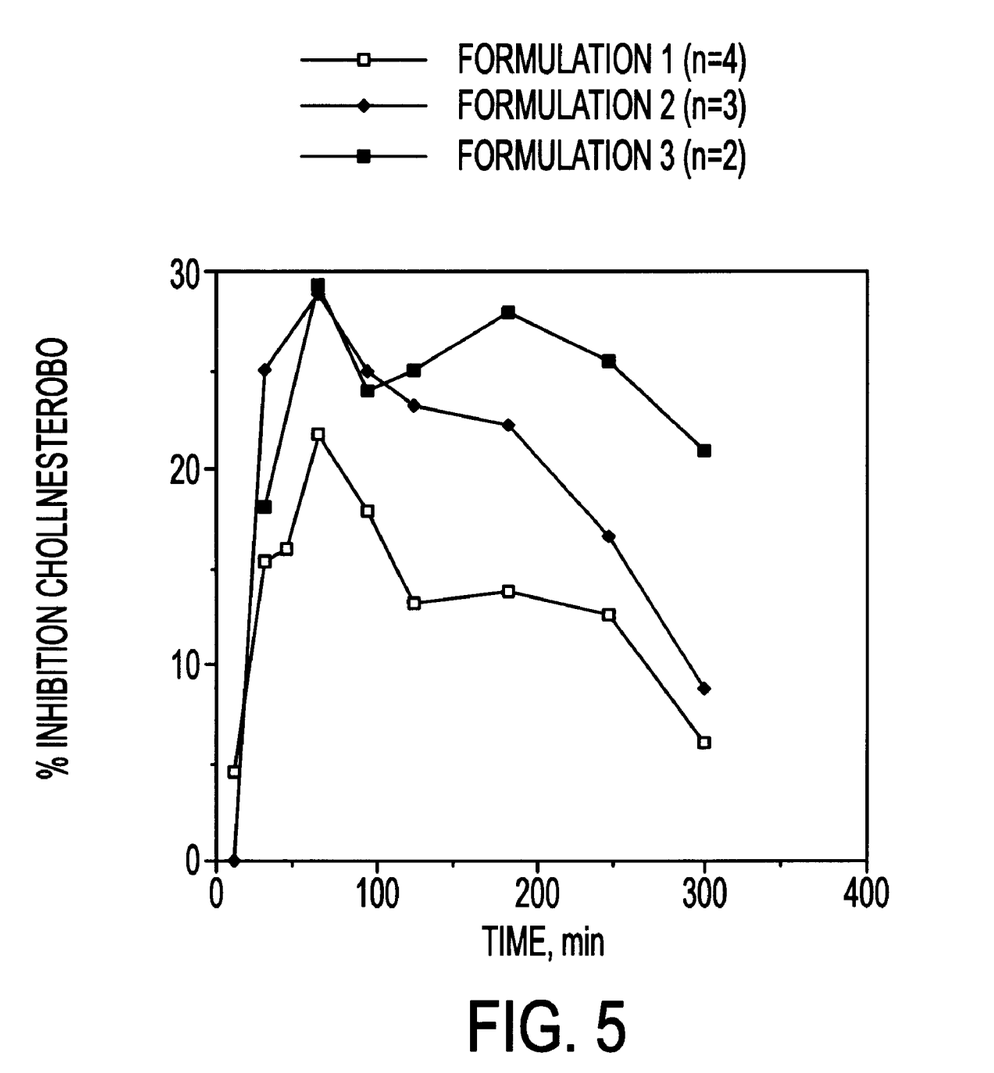
FIG. 5: shows the results of an experiment in which the inhibition of cholinesterase versus time following a PO administration of three different formulations of physostigmine.
Figure 6:
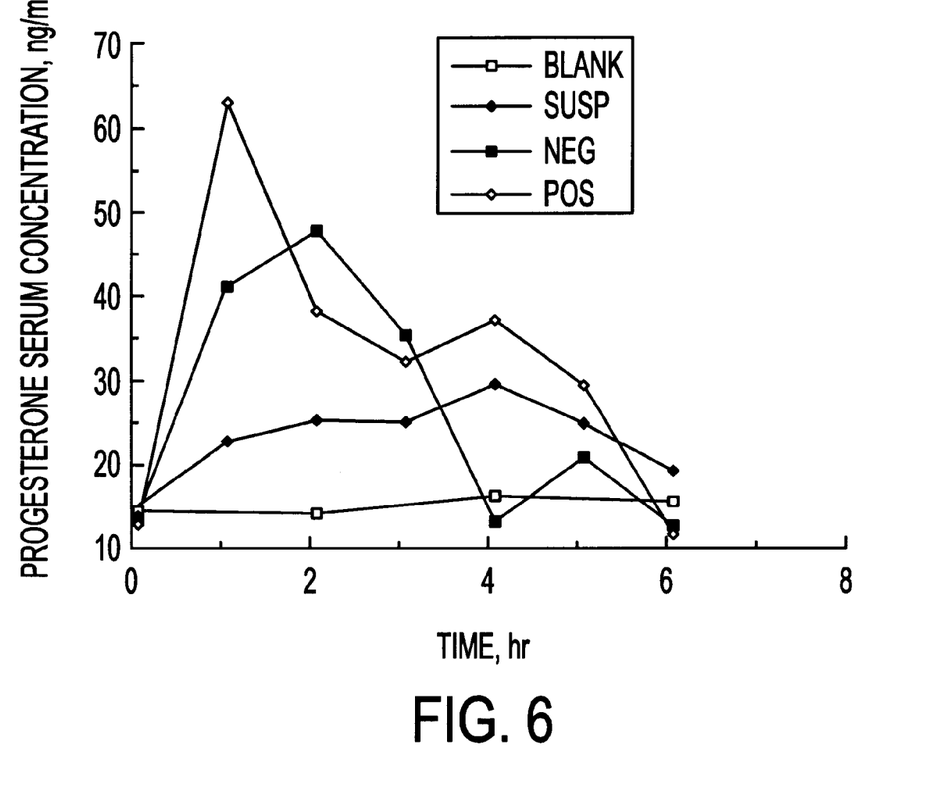
FIG. 6: shows Progesterone serum concentrations, following administration of positive and negative SEOF, containing the drug, as well as Exp.Progesterone suspension in water and blank formulation.

The results of cholinesterase inhibition with each of the formulations are shown in FIG. 5. As can be seen, P.S dissolved in soybean oil without the addition of a cationic lipid (Formulation 1) was able to inhibit about 20% of the cholinesterase activity but the inhibition was not maintained for long periods of time. P.S dissolved in soybean oil formulation containing the cationic lipid continued to maintain above 20% inhibition of cholinesterase activity even three hours after administration of the drug. The most pronounced inhibition, of above 20% for over more than five hours was achieved with the use of Arachis oil as the oily carrier in combination with the cationic lipid.

EXAMPLE VIII

Effect of orally administered insulin on glucose level in diabetic rats

Experimental methods:

Sabra male rats weighing 200 g were injected i.p with streptozocin at a dosage of 100 mg/kg, prepared by dissolving streptozocin in saline. The pH of the saline was adjusted to 4,4 with 0.1 N citric acid solution.

Streptozocin affects the glucose metabolism, and at this dose depletes endogenous insulin rendering the rats diabetic. The diabetogenic effect was assessed 24 hours after injection, by monitoring glucose blood levels using Reagent Strips test: a drop of rat blood from the tail was applied on the Glucostix™ (Miles Ltd, Ames Division, Slough, England) test pads. The glucose level was determined using Glucometer II (Miles Lab, Ames Division, Elkhart, In USA) according to manufacturer instructions. It should be emphasized that the maximum limit of the glucometer is 400 mg/dl.

Rats were anesthetized with ether and the abdominal area was shaven. Using a scalpel, a small opening was made in the abdomenal muscles and peritoneum, and the jejunal area of the intestines was exposed and wetted with saline.

The various lipid formulations were first diluted with double distilled water (1:5), gently mixed and immediately injected into the jejunum (1 ml of the resulting final emulsion containing 1 mg of insulin). The preparations were diluted prior to administration in view of the lack of fluids in the rat. The peritoneum muscles and skin were then sutured. Time 'O' was taken before drug administration. The remainder of the experiment was carried out while animals were awake and blood was withdrawn from the rat tail at given time intervals.

The tested formulations were the following:

Positive formulation: the SEOF insulin formulation shown in Table VI (n°4), which yielded positively charged emulsion droplets.

Negative formulation: the same formulation as the positive formulation without the oleylamine, which yielded negatively charged emulsion droplets.

Blank formulation: a formulation similar to the positive formulation without insulin.

Insulin aqueous suspension: a suspension of insulin in saline

Marketed insulin preparation: insulin preparation marketed by Novo

The results are shown in the following Table IX

TABLE IX

The effect of the various lipid formulations on blood glucose levels following intra-jejunal administration
Glucose blood levels, mg/dl (% reduction*)

| Time (min) | Positive formulation N = 6 | Blank emulsion N = 3 | Insulin aqueous suspension N = 4 | Marketed regular Novo - Insutin 8 Units i.p injection N = 1 |
|---|---|---|---|---|
| 0 | >400 | >400 | >400 | >400 |
| 15 | | | | 253 (37%) |
| 45 | | | 325 (18%) | 165 (59%) |
| 60 | 260 (29%) | 390 (2.5%) | | 164 (59%) |
| 90 | 246 (31%) | 392 (2%) | 312 (13%) | |
| 120 | 237 (30%) | 374 (6.5%) | 339 (10%) | 105 (74%) |
| 150 | | 375 (6%) | | |
| 180 | 255 (25%) | 365 (9%) | 332 (12%) | 109 (73%) |
| 240 | 350 (10%) | 396 (1%) | 387 (5%) | 100 (75%) |

(*) the percentage of blood glucose levels were calculated on the basis of 400 mg/dl at time 0, even is actual levels were higher.

It can be noted from the results shown in Table IX, that the aqueous dispersion of insulin was not significantly active although some absorption did occur as a result of the huge administered dose. It should be noted that the marketed insulin solution, when injected i.p to the diabetic rats (8 units/rat) markedly reduced the blood glucose level showing the validity of the use of these rats as a comparative model.

The blank lipid formulation which comprises all the excipients except insulin did not induce any hypoglycemic effect, as expected. The positive formulation which had positively charged emulsion droplets elicted a much more effective hypoglycemic effect that those of the aqueous insulin suspension.

EXAMPLE IX

Serum progesterone concentrations, following administration of various formulations.

Progesterone is the endogenic lipophilic compound that is not administered orally because of significant first pass effect. SEOF ability of improving its oral bioavailability was tested in the present study.

Four groups of sabra female rats at the age of 24–28 days (6 rats in a group) received 3 formulations, containing Progesterone and the blank formulation. Every animal was feeded with 0.5 ml of the appropriate formulation, which contained either no drug or 4 mg of Progesterone per kg weight.

The tested formulations were following:

Blank formulation: SEOF, described in example VI (n°5), diluted 1:50 with double distilled water (DDW), without the drug.

Suspension: Progesterone, suspended in DDW

Negative formulation: SEOF, described in example VI (n°5), diluted 1:50 with DDW, without Oleyl amine Positive formulation: SEOF, described in example VI (n°5), diluted 1:50 with DDW.

Progesterone concentrations were determined by RIA, using ImmuChem™ Coated tube kit, ICN Biomedicals, Inc, Costa Miesa, Calif., USA The results are shown in FIG. 6. The pharmacokinetic parameters of Progesterone, obtained following its administration in various formulations, as well as relative bioavailability of the SEOF's in comparison to suspension are presented in Table X

TABLE X

Pharmacokinetic data of progesterone formulations

|  | Suspension | Negative emulsion | Positive emulsion |
|---|---|---|---|
| $t_{max}$ (hr) | 4 | 2 | 1 |
| $c_{max}$ (ng/ml) | 29 ± 12 | 47 ± 23 | 62 ± 21* |
| AUC** (ng.hr/ml) | 69 ± 34 | 99 ± 58 | 131 ± 47* |
| F'*** relative bioavailability |  | 1.43 | 1.88 |

*Statistically significant, p <0.05, compared to suspension formulation, according to Mann-Whitney test.
AUC was calculated using the level of 13 ng/ml as "0" level $$*F' = \frac{\text{AUC emulsion (test)}}{\text{AUC suspension (reference)}}$$

EXEMPLE X
Acute toxicity of SEOF in BALB/c mice

Acute toxicity of the formulations described in examples 2–4, was examined in BALB/c mice during 30 days. 0.5 ml of each SEOF, diluted 1:10 (more than 300-fold overdosage) and 1:100 (more than 30-fold overdosage) were injected i.p to the group of 4–6 mice. Animal's condition was inspected during several hours after the procedure and then every day up to month.

Mice that received both dilutions of SEOF, described in example II, and dilution 1:100 of formulations, described in example IV, (containing 12.5% and 30% of BA) showed no sign of intoxication. Dilution 1:10 of SEOF comprising 12.5% BA also did not cause any toxic effects. On the other hand, dilution 1:10 of the formulation, containing 30% of Benzyl alcohol was found to induce immediate neurologic shock with further partial improvement and death of the animals after several days. A half dose of the same formulation still caused neurotoxic symptoms, but mice stayed alive.

As can be seen from table XI, the same toxic effects were observed also after injection of 1.5% and 3% BA water solutions, confirming its role in formulation's 300-fold overdose toxicity.

TABLE XI

Acute toxicity of emulsified SEDDS in BALB/c mice following i.p injection

| Formulation (%, w/w) | | SEDDS dilution rate in water for injection (vol*) | Number of animals per group | % survival after 30 days | Side effects |
|---|---|---|---|---|---|
| Tw.80 | 25 | 1:10(0.5) | 6 | 84 | none |
| BA | 12.5 | | | | |
| OA | 3 | 1:100(0.5) | 6 | 100 | none |
| EO | to 100 | | | | |
| Tw. 80 | 25 | 1:10(0.5) | 6 | 0 | neurologic shock |
| BA | 30 | | | | |
| OA | 3 | 1:100(0.5) | 6 | 100 | none |
| EO | to 100 | 1:10(0.25) | 4 | 100 | neurologic shock |
| BA | 3 | 1:10(0.5) | 4 | 15 | neurologic shock |
| in water for injection | | | | | |
| BA | 1.5 | 1:10 (0.5) | 6 | 100 | neurologic shock |
| in water for injection | | | | | |

(*) Vol: volume of the resulting emulsion injected i.p
(**) Dilution 1:10: a dose 300 times larger than the expected administered dose

We claim:

1. A pharmaceutical composition comprising an orally administered drug which is either hydrophobic or of limited aqueous solubility and a self-emulsifying oily formulation (SEOF), said SEOF comprising an oily component and a surfactant,
    said SEOF being characterized in that the oily component comprises an oily carrier, a cationic lipid and a lipophilic oily fatty alcohol, the oil-in-water emulsion which is formed by mixing the SEOF with an aqueous solution having positively charged oily droplets,
    said oily carrier being one or more selected from the group consisting of a medium chain triglyceride oil (MCT) in which the hydrocarbon chain has an average chain length of 8 to 12 carbon atoms, a long chain triglyceride oil (LCT) in which the hydrocarbon chain has an average chain length of more than 12 carbon atoms, and an oily fatty acid derivative.

2. A pharmaceutical composition according to claim 1 in which the cationic lipid of said SEOF is selected from the group consisting of $C_{10}$ to $C_{24}$ fatty alkylamines and $C_{12}$ to $C_{24}$ fatty alkanoylamines.

3. A pharmaceutical composition according to claim 2 in which said cationic lipid of the SEOF is selected from the group consisting of $C_{12}$ to $C_{18}$ fatty alkylamines and $C_{12}$ to $C_{18}$ fatty alkanoylamines.

4. A pharmaceutical composition according to claim 3 in which said cationic lipid is stearylamine or oleylamine.

5. A pharmaceutical composition according to claim 1 in which said LCT is formed of one or more components of the group consisting of groundnut oil, safflower oil, sesame oil, soybean oil, cottonseed oil and olive oil.

6. A pharmaceutical composition according to claim 1 in which said oily fatty acid derivative is an ester of a fatty acid with an alkyl alcohol.

7. A pharmaceutical composition according to claim 6 in which said oily fatty acid derivative is ethyl oleate.

8. A pharmaceutical composition according to claim 1 in which said lipophilic oily fatty alcohol of the SEOF is a fatty-acid alcohol or an aryl alcohol.

9. A pharmaceutical composition according to claim 8 in which said oily fatty alcohol is oleyl alcohol, benzyl alcohol, or a combination of the two.

10. A pharmaceutical composition according to claim 8 in which said oily fatty alcohol is ethyl alcohol.

11. A pharmaceutical composition according to claim 1 in which said surfactant is a non-ionic surfactant.

12. A pharmaceutical composition according to claim 11 in which said non-ionic surfactant is Tween® or Span®.

13. A pharmaceutical composition according to claim 1 in which said drug is cyclosporin A.

14. A pharmaceutical composition according to claim 1 wherein said SEOF and drug are encapsulated in a capsule.

15. A method for the administration of an orally administered drug which is either hydrophobic or of limited aqueous solubility to a subject comprising administrating said drug in a self-emulsifying oily formulation (SEOF), said SEOF comprising an oily component and a surfactant, the SEOF being characterized in that the oily component comprises an oily carrier, a cationic lipid and a lipophilic oily fatty alcohol, the oil-in-water emulsion which is formed by mixing the SEOF with an aqueous solution having positively charged oily droplets, said oily carrier being one or more selected from the group consisting of a medium chain triglyceride oil (MCT) in which the hydrocarbon chain has an average chain length of 8 to 12 carbon atoms, a long chain triglyceride oil (LCT) in which the hydrocarbon chain has an average chain length of more than 12 carbon atoms, and an oily fatty acid derivative.

16. A method according to claim 15 wherein said drug is insulin.

17. A method according to claim 15 wherein the administration of said drug is an oral, systemic administration.

18. A method according to claim 17 wherein said SEOF and drug are encapsulated in a capsule.

19. A method according to claim 18 wherein said capsule is a soft or hard gelatin capsule.

20. A method according to claim 18 wherein said capsule is gastroprotected.

21. A process for the production of an emulsion which comprises mixing an SEOF with an aqueous solution, wherein said SEOF comprises an orally administered drug which is either hydrophobic or of limited aqueous solubility, an oily component and a surfactant, the SEOF being characterized in that the oily component comprises an oily carrier, a cationic lipid and a lipophilic oily fatty alcohol, the oil-in-water emulsion which is formed by mixing the SEOF with said aqueous solution having positively charged oily droplets, said oily carrier being one or more selected from the group consisting of a medium chain triglyceride oil (MCT) in which the hydrocarbon chain has an average chain length of 8 to 12 carbon atoms, a long chain triglyceride oil (LCT) in which the hydrocarbon chain has an average chain length of more than 12 carbon atoms, and an oily fatty acid derivative.

22. A process according to claim 21 for the preparation of an oil-in-water emulsion which contains a hydrophobic drug, the process comprising incorporating said drug into said SEOF.

* * * * *